(12) United States Patent
Chaouat et al.

(10) Patent No.: US 11,109,954 B2
(45) Date of Patent: Sep. 7, 2021

(54) ANCHOR FOR MEDICAL USE, TO BE INSERTED INTO A BONY WALL

(71) Applicants: Dedienne Sante, Mauguio (FR); Gilles Chaouat, Ozoir la Ferriere (FR); Edouard Decrette, Gauciel (FR); Gilles Cohen, Paris (FR); Marc Fischer, Boulogne Bilancourt (FR); Jean-Marc Zeitoun, Paris (FR)

(72) Inventors: Gilles Chaouat, Ozoir la Ferriere (FR); Edouard Decrette, Gauciel (FR); Gilles Cohen, Paris (FR); Marc Fischer, Boulogne Bilancourt (FR); Jean-Marc Zeitoun, Paris (FR); Damien Lefief, Poulx (FR)

(73) Assignees: Dediene Sante, Mauguio (FR); Gilles Chauouat, Ozoir la Ferriere (FR); Edouard DeCrete, Gauciel (FR); Gilles Cohen, Paris (FR); Marc Fischer, Boulogne (FR); Jean-Marc Zeitoun, Paris (FR)

( * ) Notice: Subject to any disclaimer, the term of this patent is extended or adjusted under 35 U.S.C. 154(b) by 406 days.

(21) Appl. No.: 16/082,948

(22) PCT Filed: Mar. 9, 2017

(86) PCT No.: PCT/IB2017/051396
§ 371 (c)(1),
(2) Date: Sep. 7, 2018

(87) PCT Pub. No.: WO2017/153949
PCT Pub. Date: Sep. 14, 2017

(65) Prior Publication Data
US 2020/0297477 A1 Sep. 24, 2020

(30) Foreign Application Priority Data

Mar. 10, 2016 (FR) .................................. 16 52026
Oct. 17, 2016 (FR) .................................. 16 60055

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/044* (2013.01);
(Continued)

(58) Field of Classification Search
CPC combination set(s) only.
See application file for complete search history.

(56) References Cited

U.S. PATENT DOCUMENTS

2005/0245932 A1 11/2005 Fanton
2006/0100630 A1 5/2006 West
(Continued)

FOREIGN PATENT DOCUMENTS

| EP | 1588666 | 10/2005 |
|---|---|---|
| EP | 1917917 | 5/2008 |
| FR | 2682867 | 4/1993 |

*Primary Examiner* — Yashita Sharma
(74) *Attorney, Agent, or Firm* — Defillo & Associates, Inc; Evelyn A Defillo

(57) ABSTRACT

This anchor (1) includes two parts (2, 3) that are to be assemble: an outer part (2), forming at least a first jamming surface (16a) for jamming the suture thread (100); and an inner part (3), intended to be inserted and retained in the outer part (2), which forms a transverse conduit (21) and at least a second jamming surface (25) for jamming the suture thread (100).

8 Claims, 3 Drawing Sheets

(52) U.S. Cl.
CPC ......... *A61B 2017/0414* (2013.01); *A61B 2017/0445* (2013.01); *A61F 2002/0829* (2013.01)

(56) References Cited

U.S. PATENT DOCUMENTS

| | | | |
|---|---|---|---|
| 2006/0235413 A1* | 10/2006 | Denham | ............ A61B 17/0401 606/232 |
| 2007/0005068 A1 | 1/2007 | Sklar | |
| 2008/0051836 A1 | 2/2008 | Forester | |
| 2012/0059429 A1 | 3/2012 | Voisard | |

\* cited by examiner

ANCHOR FOR MEDICAL USE, TO BE INSERTED INTO A BONY WALL

CROSS REFERENCE TO RELATED APPLICATION

This application is a national stage entry of PCT/162017/051396 filed Mar. 9, 2017, under the International Convention claiming priority over French Patent Application No. 16 52026 filed Mar. 10, 2016 and French Patent Application No. 16 60055 filed Oct. 17, 2016.

FIELD OF THE INVENTION

The present invention relates to an anchor for medical use, intended to be inserted into a bony wall.

BACKGROUND OF THE INVENTION

This anchor makes it possible to fasten one or several suture threads to a bone, in particular in order to reinsert a tendon or a ligament on a bone; it is particularly intended to make it possible to reinsert one or several tendons of the rotator cuff of the shoulder joint on a humerus.

It is well known, in various indications, to reattach a tendon or ligament on a bone using an anchor inserted into the wall of this bone, this anchor being connected to one or several suture threads that make it possible to suture the tendon or ligament to the bone.

To connect the suture thread to an anchor, it is known to provide a transverse passage arranged through the anchor, through which the suture thread is engaged. This type of assembly has the drawback of generating deteriorations in the thread during the placement of the anchor, due to the friction between the anchor and the bony wall. This deterioration may lead to breaking of this thread.

It is also known to provide a proximal ring on an anchor, to which the suture thread is knotted. This type of anchor has a significant risk of breaking of the thread at the knot.

To resolve this drawback, so-called "knotless" anchors have been designed, in which the thread is held on the anchor by pinching or jamming. The existing anchors do not, however, preclude any risk of deterioration of the thread during the placement of the anchor, particularly when the latter is screwed, or risks of sectioning of the thread at its connecting point to the anchor.

OBJECTS OF THE INVENTION

The present invention aims to resolve this essential drawback.

Furthermore, a certain number of existing anchors have a relatively uncertain resistance to pulling out. This problem in particular arises for anchors intended for the re-insertion of the tendons of the rotator cuff of the shoulder joint, in light of the significant tension exerted on the suture thread (s), and therefore on the anchor(s), by these tendons during the movement of the joint.

The present invention also aims to resolve this drawback.

The main objective of the invention is therefore to provide an anchor to which one or several suture threads can be perfectly fastened and retained, with a reduced risk of shearing or breaking of this or these thread(s).

Another aim of the invention is to provide an anchor able to be perfectly fastened to a bony wall.

SUMMARY OF THE INVENTION

The anchor in question comprises, in a manner known in itself, two parts that are to be assembled, i.e., an outer part, intended to be fastened to the bone, which forms an inner longitudinal cavity through it, and an inner part, intended to be inserted and held in said cavity of the outer part, which forms a transverse conduit passing all the way through it; at least one suture thread is intended to be engaged in said cavity through the proximal side of the outer part, to be engaged through said transverse conduit and to emerge from said outer part, through said proximal side.

According to the invention, the outer part forms at least one first jamming surface arranged in the longitudinal direction of the outer part and the inner part forms at least one second jamming surface located on the proximal side relative to the transverse conduit that it comprises, this second jamming surface being arranged in the longitudinal direction of the inner part;

said at least one suture thread is intended to extend along said first jamming surface and along said second jamming surface;

the inner part is movable relative to the outer part between a distal position not blocking the suture thread, in which said second jamming surface is at a distance from said first jamming surface not performing any jamming of this thread, and a proximal blocking position of the suture thread, in which said second jamming surface is at a distance from said first jamming surface performing jamming of this thread.

It will be understood that the terms "proximal" and "distal" used above and throughout the present description are to be considered, traditionally, relative to the insertion direction of the anchor into a bony wall, the term "proximal" designating a location closer to a practitioner relative to this insertion direction and "distal" designating a location further from this practitioner relative to this same insertion direction.

The invention provides an anchor in which the strands of the suture thread(s) are located inside the anchor during the placement of the anchor and are therefore preserved from deteriorations, which would otherwise be generated by the walls of the anchor and of the bone during this placement. The outer part can then outwardly comprise a structure allowing reinforced anchoring to the bone; this may involve anchoring ribs having a significant height, and/or a noncircular cross-section of the outer part, in particular oblong, causing the outer part to be able, in a first angular position, to be engaged in a receiving hole arranged in the bone, then to be pivoted forcibly in this hole, to another angular position, offset by about ninety degrees relative to said first angular position, so as to jam the anchor in the hole.

Before placement of the anchor, the inner part may not be assembled to the outer part, causing each suture thread to be able to be engaged easily on the anchor.

Once the anchor is placed on the bone, a pulling force exerted on the strands of the suture thread(s) makes it possible to move the inner part relative to the outer part toward said proximal blocking position, producing blocking of this or these thread(s) by jamming between said first and second jamming surfaces.

These jamming surfaces, arranged longitudinally, make it possible to exert pressure on a relatively significant portion of the thread(s), providing perfect jamming of this or these threads, without risk of shearing.

Preferably, said outer part comprises two said first jamming surfaces, diametrically opposite, and said inner part comprises two corresponding said second jamming surfaces.

Thus, the two strands of each suture thread are jammed in the anchor by two pairs of jamming surfaces, one located before the passage of the thread(s) through said transverse conduit, the other located after this passage.

Preferably, at least one of said first and second jamming surfaces is inclined relative to the longitudinal axis of the anchor.

The jamming of the suture thread(s) is thus done by gradual reduction, during the movement of said inner part toward said proximal blocking position, of the space existing between said first and second jamming surfaces.

Preferably, said outer part forms at least a first engagement surface, separate from said first jamming surface, and said inner part forms at least one second engagement surface, separate from said second jamming surface, these respective engagement surfaces mutually engaging in said proximal blocking position and immobilizing said inner part relative to said outer part in this position.

A risk of said inner part returning to said distal nonblocking position is thus eliminated.

Preferably, these first and second engagement surfaces are inclined relative to the longitudinal axis of the anchor so as to be able, when the inner part is moved in the proximal direction inside the outer part, to enter a mutual jamming state that determines said proximal blocking position, and said respective jamming surfaces are arranged such that, in this proximal blocking position, a space exists between them, the thickness of which is about 10 to 40% of the diameter of a suture thread.

The engagement surfaces are thus arranged such that their mutual jamming takes place before said respective jamming surfaces perform an excessive crushing of the suture thread(s). In this way, the risk of such excessive crushing is eliminated.

According to one preferred embodiment of the invention, said outer part and said inner part have respective means for angular positioning of said inner part in said outer part, placing said transverse conduit of the inner part in a determined angular position relative to the outer part;

said outer part has a female conical cavity in which two diametrically opposite conduits are arranged, for passage of the strands of the suture thread(s) intended to be connected to the anchor; these conduits are arranged over a diameter that is parallel to the axis of said transverse conduit when said inner part is in said determined angular position; the walls delimiting these conduits on the radially outer side of the outer part forms said first jamming surfaces; the surfaces delimiting said female conical cavity between these conduits form two said first engagement surfaces;

said inner part has a male frustoconical portion from which two diametrically opposite bosses protrude; these bosses are arranged over a diameter parallel to the axis of said transverse conduit; these bosses are intended to engage in said conduits during the movement of said inner part from said distal nonblocking position to said proximal blocking position, and to jam the strands of the suture thread(s) between them and said walls delimiting the conduits toward the outside in the radial direction; the bosses make up said second jamming surfaces, and the surfaces of said male frustoconical portion located outside these bosses form two said second engagement surfaces, intended to engage with said first engagement surfaces in said proximal blocking position.

Said respective positioning means can in particular be made up of two diametrically opposite longitudinal slots arranged in said outer part and corresponding ribs arranged on the inner part, these ribs forming pads intended to be received in the guideway formed by the slots.

Advantageously, the outer part has two diametrically opposite longitudinal apertures, arranged across from the openings of said transverse conduit and extending over the entire movement of this conduit, from said distal nonblocking position to said proximal blocking position.

These apertures allow the passage of the thread(s) on either side of the inner part when this inner part has an outer diameter adjusted to the inner diameter of the cavity formed by the outer part.

Preferably, the inner part has two snapping protrusions able to snap behind the edges of the outer part delimiting the distal ends of said apertures.

Easy mounting and holding of the inner part in the outer part is thus obtained, by snapping.

Preferably, said inner part has a pointed distal portion, protruding past the outer part, on the distal side, when said inner part is in said distal nonblocking position.

This pointed distal end favors the insertion and progression of the anchor in the hole of the bony wall.

The invention, as described above, will be well understood, and other features and advantages thereof will appear, in reference to the appended schematic drawing, which shows, by way of non-limiting example, one preferred embodiment of the anchor in question.

DESCRIPTION OF THE PREFERRED EMBODIMENTS

Figure 1:
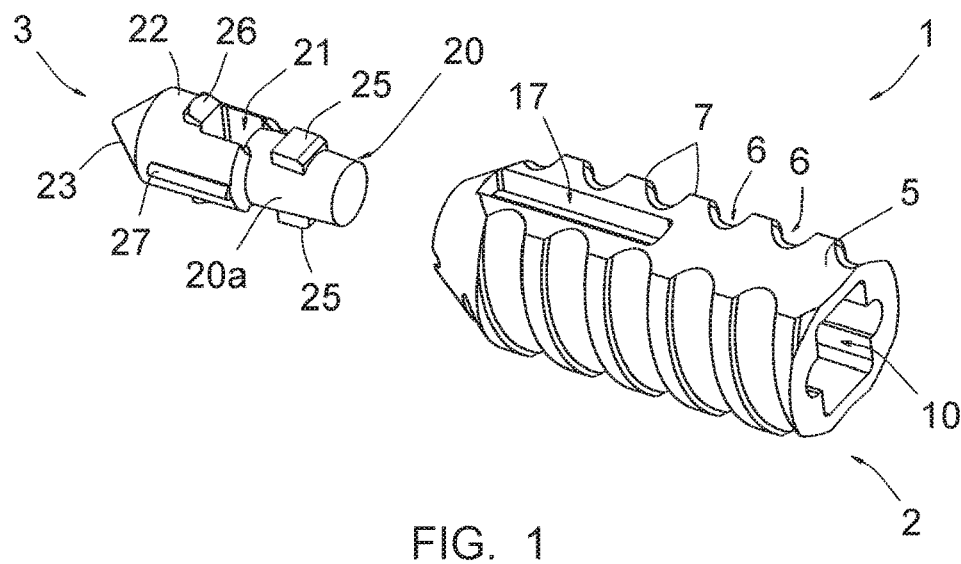
FIG. 1 is a perspective view, with an inner part that it comprises in a deployed position relative to an outer part that it also comprises.
Figure 2:
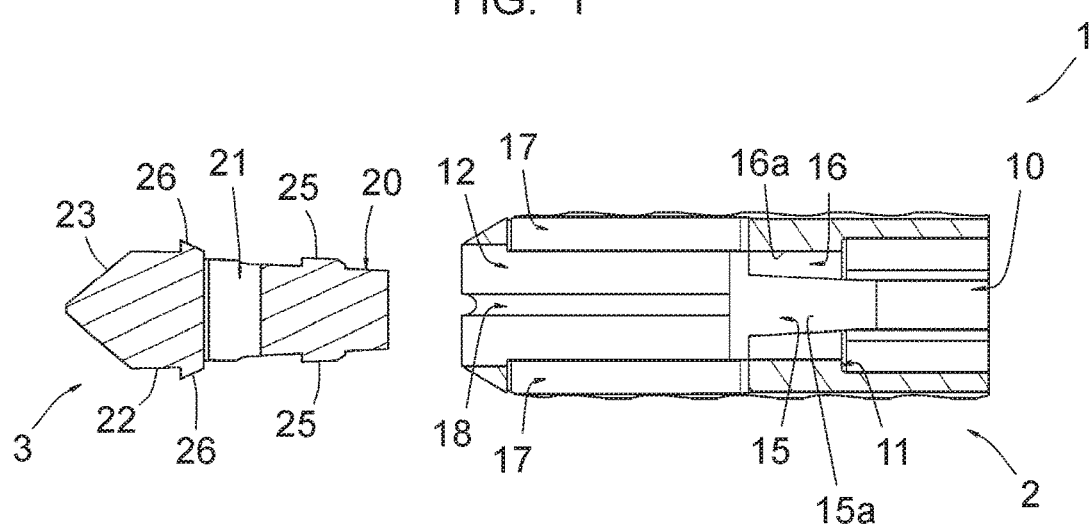
FIG. 2 is a longitudinal sectional view in a median plane passing through the axis of the transverse conduit formed by said inner part, this inner part being deployed relative to said outer part.
Figure 3:
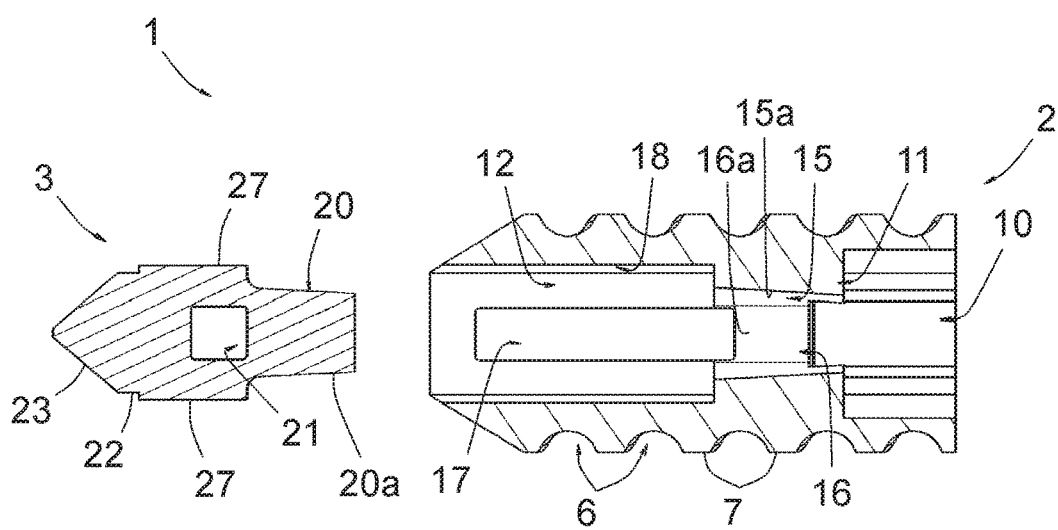
FIG. 3 is a view thereof similar to FIG. 2, along a cutting plane perpendicular to that according to FIG. 2.

FIGS. 1 to 3 show an anchor 1 for medical use, intended to be inserted into a bony wall and thus to fasten one or several suture threads 100 to this bone. This anchor 1 is in particular intended to make it possible to reinsert, on a humerus, one or several tendons of the rotator cuff of the shoulder joint.

The anchor 1 comprises an outer part 2 and an inner part 3 that are intended to be assembled to one another.

The outer part 2 is intended to be fastened to the bone. Aside from a conical distal portion, it has a cross-section in the form of a flattened ring, causing it to have two flats 5 on two opposite sides and two curved faces between these flats 5. In these curved faces, series of deep cannulations 6 are arranged, delimiting series of ribs 7 between them. The part 2 is able, in a first angular insertion position in a hole arranged in the bone wall, to be engaged in this hole, then to be pivoted forcibly in this hole, up to another angular position, offset by about ninety degrees relative to said first angular position, so as to jam the anchor 1 in the hole.

The outer part 2 forms an inner longitudinal cavity passing all the way through it, delimiting a proximal cavity 10, an intermediate portion 11 and a distal cavity 12.

Figure 4:
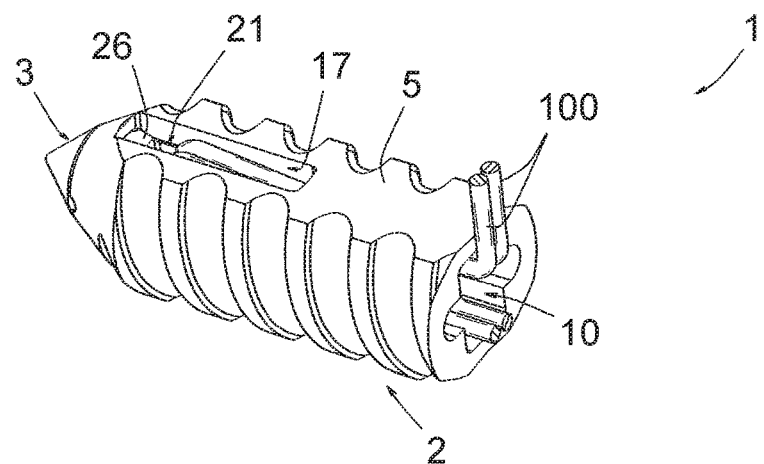
FIG. 4 is a view thereof similar to FIG. 1, after placement of suture threads and with the inner part placed in the outer part, this inner part being in a distal nonblocking position of the suture threads.

The proximal portion 10 forms, along the flats 5, two lateral housings intended to receive the suture threads, as visible in FIG. 4, and a central mounting cavity including two lateral slots, intended to receive, in a fitted manner, the distal end of the bar 101, with the corresponding section.

The intermediate portion 11 delimits a female conical cavity 15 having a gentle slope of about 5 to 10 degrees, this cavity 15 being able to receive in it, with jamming, a male frustoconical portion 20 comprised by the inner part 3, described later. It forms two diametrically opposite conduits 16, located below the flats 5 and situated in the extension of the two aforementioned lateral housings formed by the cavity 10. These conduits 16 communicate with these lateral housings and with the distal cavity 12, as visible in FIG. 2, and thus allow the strands of the suture threads 100 to pass through them, as visible in FIG. 5.

FIG. 2 shows that the walls 16*a* delimiting the bottoms of these conduits 16 are parallel to the longitudinal axis of the outer part 2.

The distal cavity 12 communicates with the outside of the part 2 by two apertures 17, extending through the flats 5, and forms two diametrically opposite slots 18, extending in a diametric plane perpendicular to the plane in which the apertures 17 extend.

The inner part 3 is intended to be inserted and held in the distal cavity 12 and in the female cavity 15 of the outer part 2. From the proximal side to the distal side, it has the aforementioned male frustoconical portion 20, a portion traversed by a transverse conduit 21, a snapping portion 22 and a distal portion 23.

The male frustoconical portion 20 has a slope corresponding to that of said female cavity 15, so as to be able to be received with jamming in this cavity. It forms a proximal face perpendicular to its longitudinal axis, against which the rod 102 sliding in the bar 101 is able to bear, as described later. It also has two diametrically opposite bosses 25, arranged on a diameter of the portion 20 parallel to the axis of the transverse conduit 21; these bosses 25 are intended to engage in said conduits 16 during the passage of the inner part 3 from the nonblocking distal position shown in FIGS. 5 and 6 to the proximal blocking position shown in FIGS. 7 and 8, thus jamming the strands of the suture threads 100 between them and the walls 16*a* forming the bottoms of the conduits 16.

The transverse conduit 21 passes all the way through the inner part 3 and has a square cross-section in the illustrated example. It is intended to be traversed by the suture threads 100, as shown in FIGS. 5 to 8.

Figure 5:
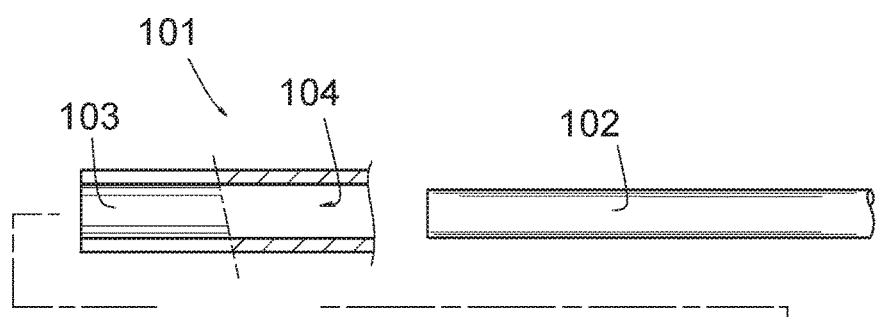
FIG. 5 is a view thereof similar to FIG. 4, according to a cutting plane identical to that according to FIG. 2; this FIG. 5 also shows an end portion of the bar and a portion of a rod comprised by an instrument used to place the anchor in a bony wall; the end portion of the bar is shown partially in longitudinal sectional view and partially in outside view.
Figure 5:
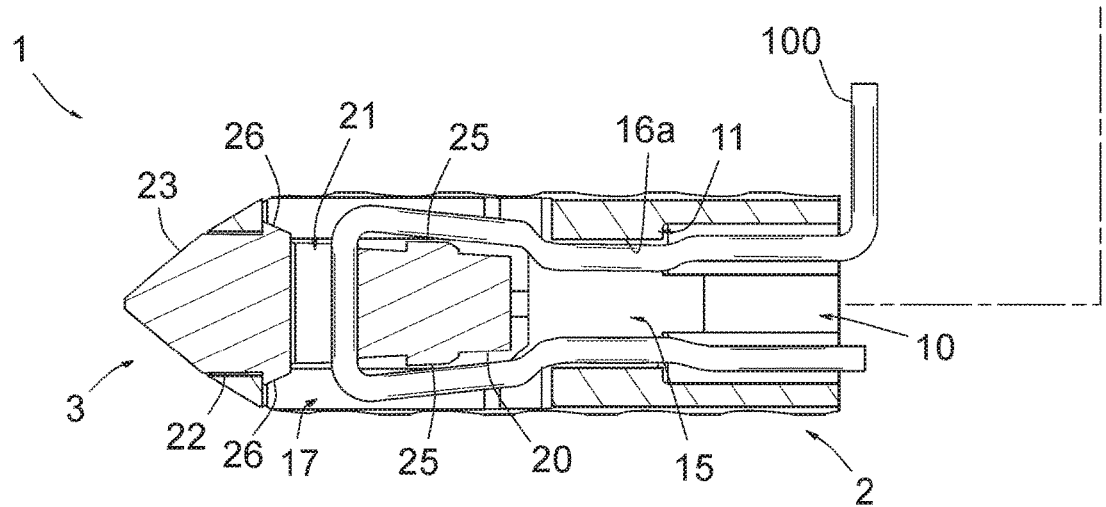

The snapping portion 22 has two snapping protrusions 26 able to snap behind the edges of the outer part 2 delimiting the distal ends of the apertures 17, as shown in FIG. 5.

The conical distal portion 23 is pointed and its peripheral wall comes, in the nonblocking distal position shown in FIG. 5, into the extension of the wall of the conical distal portion of the outer part 2.

Figure 6:
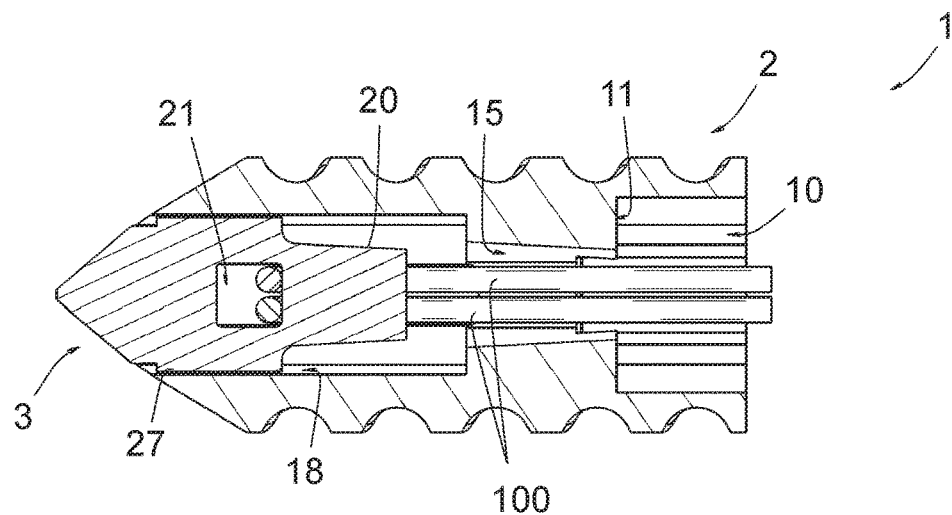
FIG. 6 is a view of the anchor similar to FIG. 4, in a cutting plane identical to that according to FIG. 3.
Figure 8:
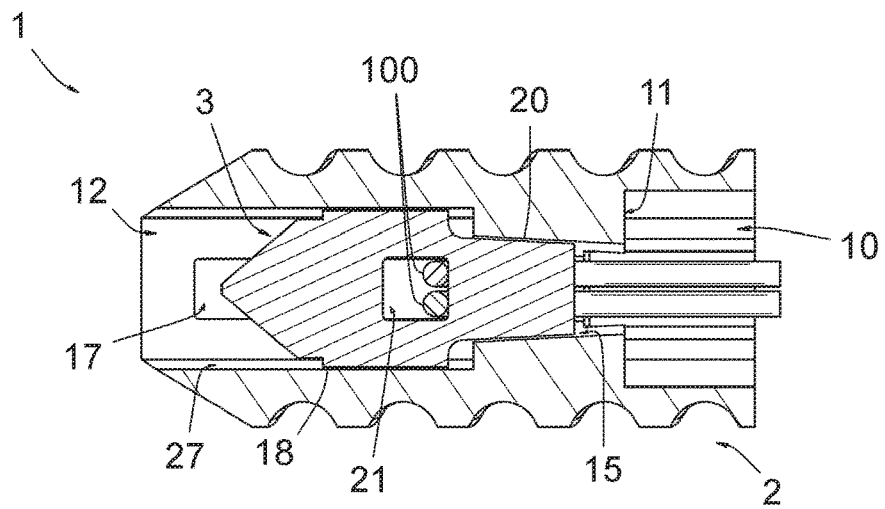
FIG. 8 is a view thereof similar to FIG. 7, along a cutting plane identical to that according to FIG. 3.

Furthermore, the inner part 3 forms, on its portion delimiting the conduit 21 and on its snapping portion 22, two diametrically opposite elongated ribs 27, located in a plane perpendicular to the plane in which the axis of the conduit 21 extends. These ribs 27 form pads intended to be received in the guideway formed by the slots 18, as shown in FIGS. 6 and 8.

The instrument partially shown in FIG. 5 is according to that described by French patent application publication no. 16 52026. The bar 101 has a square cross-section and, as shown in FIG. 5, at its distal end portion, two lateral ribs 103. This distal portion of the bar 101 is suitable for being engaged in the aforementioned mounting cavity formed by the proximal cavity 10, with the ribs 103 received in the aforementioned two lateral slots of this cavity.

The bar 101 is pierced longitudinally with a bore 104 in which the aforementioned rod 102 is engaged slidingly. The rod 102 is movable in this bore 104 between the distal position, in which it bears against the proximal face of the inner part 3 while the bar 101 is inserted into said mounting cavity, and a proximal position, in which it is withdrawn with respect to this proximal face. In this distal position, the rod 102 keeps the inner part 3 in the distal nonblocking position and, in its proximal position, does not hinder the movement of the inner part 3 toward the proximal blocking position visible in FIGS. 7 and 8.

The instrument comprises means (not shown, described in French patent application publication no. 16 52026) making it possible to selectively block the rod 102 with respect to the bar 101, in said distal position of this rod. These means can in particular be in the form of a slide transversely supported by a sleeve secured to the bar 101, this slide being movable transversely to the longitudinal axis of this bar 101; the slide has a solid wall portion and a wall portion pierced with a hole having a section larger than that of the rod 102; in a sliding position, said solid wall portion of this slide is located in the immediate vicinity of the proximal end of the rod 102 and thus blocks any withdrawal of this rod, and in another sliding position of this slide, the hole formed by this slide is located across from the rod 102 and allows the withdrawal of this rod.

In practice, the suture threads 100 are engaged through the outer part 2, then through the transverse conduit 21, then again through the outer part 2, and the inner part 3 is engaged in the distal cavity 12, with the ribs 27 in the slots 18, until snapping of the protrusions 26 beyond the edges of the part 2 delimiting the distal ends of the apertures 17. The anchor 1 is then in the state visible in FIGS. 4 to 6.

To carry out the insertion of the anchor 1 into a bone cavity, the free end portion of the bar 101 is engaged in said mounting cavity and the rod 102 is blocked in its distal position, thus keeping the inner part 3 in said distal nonblocking position visible in FIGS. 5 and 6.

Figure 7:
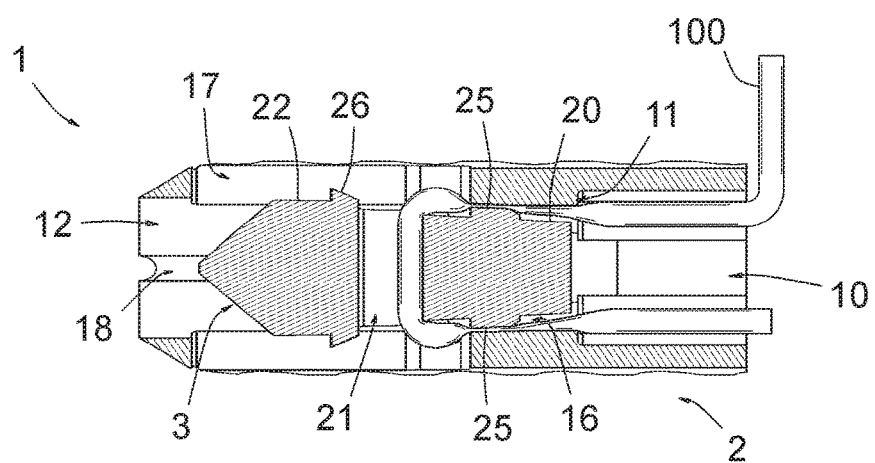
FIG. 7 is a view thereof with said inner part in a proximal blocking position of the suture threads, in a cutting plane identical to that according to FIG. 2.

Once the insertion of the anchor 1 into the bone is done, the withdrawal of the rod 102 is unblocked, which allows the inner part 3 to move toward the proximal blocking position visible in FIGS. 7 and 8 when a pulling force is exerted on the threads 100, in particular when the ligaments are put back into place on the bone. In this position, the suture threads 100 are pinched between the bottoms 16*a* of the conduits 16 and the radially outer faces of the bosses 25, these bottoms and faces making up respective jamming surfaces of the threads 100.

Simultaneously, the parts of the male frustoconical portion 20 not across from the conduits 16 engage in the parts of the cavity 15 located outside the conduits 16, until jamming, providing immobilization of the inner part 3 relative to the outer part 2 in this proximal position.

The invention provides an anchor for medical use having decisive advantages relative to the counterpart anchors of the prior art, in particular those of:

preserving the strands of the suture thread(s) 100 from deteriorations resulting from the placement of the anchor, due to the fact that these threads are placed inside the anchor 1;

outwardly comprising a structure allowing perfect anchoring of the anchor 1 in a bone, in particular by jamming resulting from pivoting by a quarter-revolution;

preserving a relatively easy placement of the suture thread(s) in it, due to its structure in two assemblable parts 2, 3;

having an easy assembly of these two parts;

making it possible to exert pressure on a relatively large portion of the suture thread(s) 100, providing perfect jamming of this or these threads, without risk of shearing.

The anchor 1 has been described above in reference to a preferred embodiment; of course, this description is in no way limiting.

The invention claimed is:

1. An anchor (1) for medical use, intended to be inserted into a bony wall, comprising:
    an outer part having a proximal side and a longitudinal direction, intended to be fastened to the bone, which forms an inner longitudinal cavity therethrough; and
    an inner part having a longitudinal direction, intended to be inserted and held in said cavity of the outer part, which forms a transverse conduit passing all the way through it;
    having an axis; at least one suture thread is intended to be engaged in said cavity through the proximal side of the outer part, to be engaged through said transverse conduit and to emerge from said outer part, through said proximal side;
    wherein:
    the outer part forms at least one first jamming surface arranged in the longitudinal direction of the outer part and the inner part forms at least one second jamming surface located on the proximal side relative to the transverse conduit that it comprises, the second jamming surface being arranged in the longitudinal direction of the inner part;
    said at least one suture thread is intended to extend along said first jamming surface and along said second jamming surface;
    the inner part is movable relative to the outer part between a distal position not blocking the suture thread, in which said second jamming surface is at a distance from said first jamming surface not performing any jamming of this thread, and a proximal blocking position of the suture thread, in which said second jamming surface is at a distance from said first jamming surface performing jamming of the thread;
    wherein said outer part comprises two said first jamming surfaces, diametrically opposite, and said inner part comprises two corresponding said second jamming surfaces; and
    wherein at least one of said first and second jamming surfaces is inclined relative to the longitudinal axis of the anchor.

2. The anchor according to claim 1, wherein said outer part forms at least a first engagement surface, separate from said first jamming surface, and in that said inner part forms at least one second engagement surface, separate from said second jamming surface, these respective engagement surfaces mutually engaging in said proximal blocking position and immobilizing said inner part relative to said outer part in this position.

3. The anchor according to claim 1, wherein the outer part has two diametrically opposite longitudinal apertures, arranged across from the openings of said transverse conduit and extending over the entire movement of the conduit, from a distal nonblocking position to said proximal blocking position.

4. The anchor according to claim 1, wherein said inner part has a pointed distal portion, protruding past the outer part, on the distal side, when said inner part is in said distal nonblocking position.

5. An anchor (1) for medical use, intended to be inserted into a bony wall, comprising:
    an outer cart having a proximal side and a longitudinal direction, intended to be fastened to the bone, which forms an inner longitudinal cavity therethrough; and
    an inner part having a longitudinal direction, intended to be inserted and held in said cavity of the outer part which forms a transverse conduit passing all the way through it; having an axis; at least one suture thread is intended to be engaged in said cavity through the proximal side of the outer cart, to be engaged through said transverse conduit and to emerge from said outer part, through said proximal side;
    wherein:
    the outer part forms at least one first jamming surface arranged in the longitudinal direction of the outer part and the inner part forms at least one second jamming surface located on the proximal side relative to the transverse conduit that it comprises, the second jamming surface being arranged in the longitudinal direction of the inner part;
    said at least one suture thread is intended to extend along said first jamming surface and along said second jamming surface;
    the inner part is movable relative to the outer part between a distal position not blocking the suture thread, in which said second jamming surface is at a distance from said first jamming surface not performing any jamming of this thread, and a proximal blocking position of the suture thread, in which said second jamming surface is at a distance from said first jamming surface performing jamming of the thread;
    wherein said outer part forms at least a first engagement surface, separate from said first jamming surface, and in that said inner part forms at least one second engagement surface, separate from said second jamming surface, these respective engagement surfaces mutually engaging in said proximal blocking position and immobilizing said inner part relative to said outer part in the position;
    wherein said first and second engagement surfaces are inclined relative to the longitudinal axis of the anchor so as to be able, when the inner part is moved in the proximal direction inside the outer part, to enter a mutual jamming state that determines said proximal blocking position, and said respective jamming surfaces are arranged such that, in the proximal blocking position, a space exists between them, the thickness of which is about 10 to 40% of the diameter of a suture thread.

6. An anchor (1) for medical use, intended to be inserted into a bony wall, comprising:
- an outer part having a proximal side and a longitudinal direction, intended to be fastened to the bone, which forms an inner longitudinal cavity therethrough; and
- an inner part having a longitudinal direction, intended to be inserted and held in said cavity of the outer part, which forms a transverse conduit passing all the way through it; having an axis; at least one suture thread is intended to be engaged in said cavity through the proximal side of the outer part, to be engaged through said transverse conduit and to emerge from said outer part, through said proximal side;

wherein:
- the outer part forms at least one first jamming surface arranged in the longitudinal direction of the outer part and the inner part forms at least one second jamming surface located on the proximal side relative to the transverse conduit that it comprises the second jamming surface being arranged in the longitudinal direction of the inner part;
- said at least one suture thread is intended to extend along said first jamming surface and along said second jamming surface;
- the inner part is movable relative to the outer part between a distal position not blocking the suture thread, in which said second jamming surface is at a distance from said first jamming surface not performing any jamming of the thread, and a proximal blocking position of the suture thread, in which said second jamming surface is at a distance from said first jamming surface performing jamming of the thread;
- wherein said outer part forms at least a first engagement surface, separate from said first jamming surface, and in that said inner part forms at least one second engagement surface, separate from said second jamming surface, these respective engagement surfaces mutually engaging in said proximal blocking position and immobilizing said inner part relative to said outer part in the position;

wherein:
- said outer part and said inner part have respective devices for angular positioning of said inner part in said outer part, placing said transverse conduit of the inner part in a determined angular position relative to the outer part;
- said outer part has a female conical cavity, in which two diametrically opposite conduits are arranged, for passage of the strands of the suture threads intended to be connected to the anchor; these conduits are arranged over a diameter that is parallel to the axis of said transverse conduit when said inner part is in said determined angular position; the walls delimiting these conduits on the radially outer side of the outer part forms said first jamming surfaces; the surfaces delimiting said female conical cavity between these conduits form two said first engagement surfaces;
- said inner part has a male frustoconical portion from which two diametrically opposite bosses protrude; these bosses are arranged over a diameter parallel to the axis of said transverse conduit; these bosses are intended to engage in said conduits during the movement of said inner part from said distal nonblocking position to said proximal blocking position, and to jam the strands of the suture threads between them and said walls delimiting the conduits toward the outside in the radial direction; the bosses make-up said second jamming surfaces, and the surfaces of said male frustoconical portion located outside these bosses form two said second engagement surfaces, intended to engage with said first engagement surfaces in said proximal blocking position.

7. An anchor (1) for medical use, intended to be inserted into a bony wall, comprising:
- an outer part having a proximal side and a longitudinal direction, intended to be fastened to the bone, which forms an inner longitudinal cavity therethrough; and
- an inner part having a longitudinal direction, intended to be inserted and held in said cavity of the outer part, which forms a transverse conduit passing all the way through it; having an axis; at least one suture thread is intended to be engaged in said cavity through the proximal side of the outer part, to be engaged through said transverse conduit and to emerge from said outer part through said proximal side;

wherein:
- the outer part forms at least one first jamming surface arranged in the longitudinal direction of the outer part and the inner part forms at least one second jamming surface located on the proximal side relative to the transverse conduit that it comprises, the second jamming surface being arranged in the longitudinal direction of the inner part;
- said at least one suture thread is intended to extend along said first jamming surface and along said second jamming surface;
- the inner part is movable relative to the outer part between a distal position not blocking the suture thread, in which said second jamming surface is at a distance from said first jamming surface not performing any jamming of the thread, and a proximal blocking position of the suture thread, in which said second jamming surface is at a distance from said first jamming surface performing jamming of the thread;
- wherein said outer part forms at least a first engagement surface, separate from said first jamming surface, and in that said inner part forms at least one second engagement surface, separate from said second jamming surface, these respective engagement surfaces mutually engaging in said proximal blocking position and immobilizing said inner part relative to said outer part in the position;

wherein:
- said outer part and said inner part have respective devices for angular positioning of said inner part in said outer part, placing said transverse conduit of the inner part in a determined angular position relative to the outer part;
- said outer part has a female conical cavity, in which two diametrically opposite conduits are arranged, for passage of the strands of the suture threads intended to be connected to the anchor; these conduits are arranged over a diameter that is parallel to the axis of said transverse conduit when said inner part is in said determined angular position; the walls delimiting these conduits on the radially outer side of the outer part forms said first jamming surfaces; the surfaces delimiting said female conical cavity between these conduits form two said first engagement surfaces;
- said inner part has a male frustoconical portion from which two diametrically opposite bosses protrude; these bosses are arranged over a diameter parallel to the axis of said transverse conduit; these bosses are intended to engage in said conduits during the movement of said inner part from said distal nonblocking position to said proximal blocking position, and to jam the strands of the suture threads between them and said walls delimiting the conduits toward the outside in the radial direction; the bosses make-up said second jamming surfaces, and the surfaces of said male frustoconical portion located outside these bosses form two said second engagement surfaces, intended to engage with said first engagement surfaces in said proximal blocking position;

wherein the positioning device is made up of two diametrically opposite longitudinal slots arranged in said outer part and corresponding ribs arranged on the inner part, these ribs forming pads intended to be received in the guideway formed by the slots.

8. An anchor (1) for medical use, intended to be inserted into a bony wall, comprising:

an outer part having a proximal side and a longitudinal direction, intended to be fastened to the bone, which forms an inner longitudinal cavity therethrough; and an inner part having a longitudinal direction, intended to be inserted and held in said cavity of the outer part, which forms a transverse conduit passing all the way through it; having an axis; at least one suture thread is intended to be engaged in said cavity through the proximal side of the outer part, to be engaged through said transverse conduit and to emerge from said outer part through said proximal side;

wherein:

the outer part forms at least one first jamming surface arranged in the longitudinal direction of the outer part and the inner part forms at least one second jamming surface located on the proximal side relative to the transverse conduit that it comprises, the second said at least one suture thread is intended to extend along said first jamming surface and along said second jamming surface;

said at least one suture thread is intended to extend along said first jamming surface and along said second jamming surface;

the inner part is movable relative to the outer part between a distal position not blocking the suture thread, in which said second jamming surface is at a distance from said first jamming surface not performing any jamming of the thread, and a proximal blocking position of the suture thread, in which said second jamming surface is at a distance from said first jamming surface performing jamming of the thread;

wherein the outer part has two diametrically opposite longitudinal apertures, arranged across from the openings of said transverse conduit and extending over the entire movement of the conduit, from a distal non-blocking position to said proximal blocking position;

wherein the inner part has two snapping protrusions able to snap behind the edges of the outer part delimiting the distal ends of said apertures.

* * * * *